(12) United States Patent
Tobinick

(10) Patent No.: US 6,177,077 B1
(45) Date of Patent: *Jan. 23, 2001

(54) TNT INHIBITORS FOR THE TREATMENT OF NEUROLOGICAL DISORDERS

(76) Inventor: Edward L. Tobinick, 100 UCLA Medical Plaza, Suite 205, Los Angeles, CA (US) 90024-6903

( * ) Notice: Under 35 U.S.C. 154(b), the term of this patent shall be extended for 0 days.

This patent is subject to a terminal disclaimer.

(21) Appl. No.: 09/476,643

(22) Filed: Dec. 31, 1999

Related U.S. Application Data

(63) Continuation-in-part of application No. 09/275,070, filed on Mar. 23, 1999, now Pat. No. 6,015,557, which is a continuation-in-part of application No. 09/256,388, filed on Feb. 24, 1999, now abandoned.

(51) Int. Cl.⁷ .................................................. A61K 39/395
(52) U.S. Cl. ............................................................. 424/134.1
(58) Field of Search ........................................... 424/134.1

(56) References Cited

U.S. PATENT DOCUMENTS

| | | |
|---|---|---|
| 5,574,022 | 11/1996 | Roberts et al. . |
| 5,605,690 | 2/1997 | Jacobs et al. . |
| 5,650,396 | 7/1997 | Carlino et al. . |
| 5,656,271 | 8/1997 | Le et al. . |
| 5,756,482 | 5/1998 | Roberts et al. . |
| 5,962,481 * | 10/1999 | Levin et al. .......................... 514/352 |

* cited by examiner

*Primary Examiner*—William R. A. Jarvis
(74) *Attorney, Agent, or Firm*—Ezra Sutton

(57) ABSTRACT

A method is disclosed for inhibiting the action of TNF for treating neurological conditions in a human by administering a TNF antagonist for reducing the inflammation of neuronal tissue or the neuromuscular junction of a human, or for modulating the immune response affecting neuronal tissue or the neuromuscular junction of a human by administering to the human a therapeutically effective dosage level of a TNF antagonist. The TNF antagonist is selected from the group consisting of etanercept, infliximab, pegylated soluble TNF receptor Type I (PEGsTNF-R1), other agents containing soluble TNF receptors, CDP571 (a humanized monoclonal anti-TNF-alpha antibody), other monoclonal anti-TNF-alpha antibodies, TNF-alpha converting enzyme inhibitors and D2E7 (a human anti-TNF mAb) for reducing the inflammation of neuronal tissue or the neuromuscular junction of a human, or for modulating the immune response affecting neuronal tissue or the neuromuscular junction of a human.

29 Claims, No Drawings

TNT INHIBITORS FOR THE TREATMENT OF NEUROLOGICAL DISORDERS

RELATED APPLICATION

This application is a continuation-in-part of application Ser. No. 09/275,070, filed on Mar. 23, 1999, now U.S. Pat. No. 6,015,557, which is a continuation-in-part of application Ser. No. 09/256,388, filed Feb. 24, 1999 now abandoned.

FIELD OF THE INVENTION

The present invention relates to tumor necrosis factor (TNF) antagonists or TNF blockers for the treatment of neurological disorders, trauma, injuries or compression; demyelinating neurological disorders, including multiple sclerosis; neurodegenerative diseases, including Alzheimer's disease; muscular disorders; and disorders of the optic nerve and retina (hereinafter "Neurologic and Related TNF Disorders"). More particularly, the TNF antagonists, TNF inhibitors or TNF blockers, are used for the treatment, prevention or amelioration of these "Neurologic and Related TNF Disorders" by modulating the action of TNF in the human body. The use of these TNF antagonists or TNF blockers results in the amelioration of these disorders and diseases and represents a novel use for this class of drugs.

BACKGROUND OF THE INVENTION

Neurological disorders due to demyelinating disease (e.g. multiple sclerosis), immune disease, inflammation, trauma, or compression, occur in different clinical forms depending upon the anatomic site and the cause and natural history of the physiological problem. For example, in Alzheimer's disease the brain undergoes a serious form of neurodegeneration of unknown etiology. Common to all of these disorders is the fact that they can cause permanent neurological damage, that damage can occur rapidly and be irreversible, and that current treatment of these conditions is unsatisfactory, often requiring surgery and/or the use of pharmacologic agents, which are often not completely successful.

These neurological conditions include acute spinal cord trauma, spinal cord compression, spinal cord hematoma, cord contusion (these cases are usually traumatic, such as motorcycle accidents or sports injuries); nerve compression, the most common condition being a herniated disc causing sciatic nerve compression, neuropathy, and pain; but also including cervical disc herniation, causing nerve compression in the neck; acute or chronic spinal cord compression from cancer (this is usually due to metastases to the spine, such as from prostate, breast or lung cancer); autoimmune disease of the nervous system; and demyelinating diseases, the most common condition being multiple sclerosis.

Steroid drugs such as cortisone that are used to treat many of the aforementioned neurological problems and conditions are particularly hazardous because they are used either at high dosage, with a corresponding increasing risk of side effects, or because they are used chronically, also increasing their adverse effects. Lastly, steroids are only partially effective or completely ineffective.

Tumor necrosis factor (TNF), a naturally occurring cytokine, plays a central role in the inflammatory response and in immune injury. TNF is formed by the cleavage of a precursor transmembrane protein, forming soluble molecules which aggregate to form trimolecular complexes. These complexes then bind to receptors found on a variety of cells. Binding produces an array of pro-inflammatory effects, including release of other pro-inflammatory cytokines, including interleukin (IL)-6, IL-8, and IL-1; release of matrix metalloproteinases; and up regulation of the expression of endothelial adhesion molecules, further amplifying the inflammatory and immune cascade by attracting leukocytes into extravascular tissues. TNF is now well established as key in the pathogenesis of rheumatoid arthritis (RA) and Crohn's Disease.

Specific inhibitors of TNF, only recently commercially available, now provide the possibility of therapeutic intervention in TNF mediated diseases. Dramatic therapeutic success has already been demonstrated with infliximab, a chimeric anti-TNF monoclonal antibody (mAb), in treating Crohn's Disease and RA; and with etanercept, a recombinant fusion protein consisting of two soluble TNF receptors joined by the Fc fragment of a human IgG1 molecule, in treating RA and Psoriatic Arthritis. Other specific anti-TNF agents are under development, including D2E7 (a human anti-TNF mAb), CDP 571 (a chimeric, but 95% humanized, anti-TNF mAb), and a pegylated soluble TNF type 1 receptor. Additionally, thalidomide has been demonstrated to be a potent anti-TNF agent. Further, anti-TNF therapies may include gene therapy and the development of selective inhibitors of the TNF-alpha converting enzyme.

As with other organ systems, TNF has been shown to have a key role in the central nervous system. There is a need for TNF inhibitors that will open a new realm of therapeutic possibilities for a wide variety of neurological and related disorders. These disorders are diverse and include inflammatory and autoimmune disorders of the nervous system, including multiple sclerosis, Guillain Barre syndrome, and myasthenia gravis; degenerative disorders of the nervous system, including Alzheimer's disease, Parkinson's disease and Huntington's disease; disorders of related systems of the retina and of muscle, including optic neuritis, macular degeneration, diabetic retinopathy, dermatomyositis, amyotrophic lateral sclerosis, and muscular dystrophy; and injuries to the nervous system, including traumatic brain injury, acute spinal cord injury, and stroke.

The limited ability of the body to effect repair after injury to the nervous system, the devastating nature of these diseases and the lack of effective therapy all highlight the importance of early therapy aimed at preventing or limiting neuronal destruction. Anti-TNF therapies are ideally suited to this task because they have been demonstrated to dramatically limit inflammation by interrupting the inflammatory cascade at a fundamental level.

There remains a need for a new pharmacologic treatment of these aforementioned physiological problems of the nervous system associated with autoimmune disease, demyelinating diseases, neurodegenerative diseases, trauma, injuries and compression with the pharmacological use of TNF antagonists or TNF blockers, which are greatly beneficial for the large number of patients whom these conditions affect. Drugs which are powerful TNF blockers are etanercept, infliximab, pegylated soluble TNF Receptor Type I (PEGs TNF-R1), other agents containing soluble TNF receptors, CDP571 (a humanized monoclonal anti-TNF-alpha antibodies), thalidomide, phosphodiesterase 4 (IV) inhibitor thalidomide analogues and other phosphodiesterase IV inhibitors. Etanercept or infliximab may be used for the immediate, short term and long term (acute and chronic) blockade of TNF in order to minimize neurological damage mediated by TNF dependent processes occurring in the aforementioned neurological disorders. The use of these TNF antagonists or TNF blockers would result in the amelioration of these physiological neurological problems.

Additionally, several of these TNF agents will not cross the blood-brain barrier. Accordingly, there is also a need for these TNF agents to be introduced directly into the cerebrospinal fluid to be effective. This can be accomplished either at the level of the spinal cord, or by introduction into the ventricular system of the brain, usually via an indwelling, subcutaneous reservoir which is connected by catheter into the ventricular system. This will allow the chronic use of these agents for the treatment of neurological disorders which require chronic TNF modulation.

DESCRIPTION OF THE PRIOR ART

Pharmacologic chemical substances, compounds and agents which are used for the treatment of neurological disorders, trauma, injuries and compression having various organic structures and metabolic functions have been disclosed in the prior art. For example, U.S. Pat. Nos. 5,756,482 and 5,574,022 to ROBERTS et al disclose methods of attenuating physical damage to the nervous system and to the spinal cord after injury using steroid hormones or steroid precursors such as pregnenolone, and pregnenolone sulfate in conjunction with a non-steroidal anti-inflammatory substance such as indomethacin. These prior art patents do not teach the use of a TNF antagonist or TNF blocker for the suppression and inhibition of the action of TNF in the human body to treat "Neurologic and Related TNF Disorders", as in the present invention.

U.S. Pat. No. 5,605,690 to JACOBS discloses a method for treating TNF-dependent inflammatory diseases such as arthritis by administering a TNF antagonist, such as soluble human TNFR (a sequence of amino acids), to a human. This prior art patent does not teach the use of a TNF antagonist or TNF blocker for the suppression and inhibition of the action of TNF in the human body to treat "Neurologic and Related TNF Disorders", as in the present invention.

U.S. Pat. No. 5,656,272 to LE et al discloses methods of treating TNF-alphamediated Crohn's disease using chimeric anti-TNF antibodies. This prior art patent does not teach the use of a TNF antagonist or TNF blocker for the suppression and inhibition of the action of TNF in the human body to treat "Neurologic and Related TNF Disorders", as in the present invention.

U.S. Pat. No. 5,650,396 discloses a method of treating multiple sclerosis (MS) by blocking and inhibiting the action of TNF in a patient. This prior art patent does not teach the use of TNF antagonists as in the present invention.

None of the prior art patents disclose or teach the use of the TNF antagonists or TNF blockers of the present invention for suppression and inhibition of the action of TNF in a human to treat "Neurologic and Related TNF Disorders", in which the TNF antagonist gives the patient a better opportunity to heal, slows disease progression, prevents neurological damage, or otherwise improves the patient's health.

Accordingly, it is an object of the present invention to provide TNF antagonists for a new pharmacologic treatment of "Neurologic and Related TNF Disorders", such that the use of these TNF antagonists will result in the amelioration of these conditions.

Another object of the present invention is to provide a TNF antagonist for providing suppression and inhibition of the action of TNF in a human to treat "Neurologic and Related TNF Disorders".

Another object of the present invention is to provide a TNF antagonist that reduces inflammation to the patient by inhibiting the action of TNF in the human body for the immediate, short term (acute conditions) and long term (chronic conditions), such that this reduction in inflammation will produce clinical improvement in the patient and will give the patient a better opportunity to heal, slows disease progression, prevents neurological damage, or otherwise improves the patient's health.

Another object of the present invention is to provide TNF antagonists that can offer acute and chronic treatment regimens for neurological conditions caused by neurological trauma, compression, injury and/or disease; such conditions including acute spinal cord or brain injury, herniated nucleus pulposus (herniated disc), spinal cord compression due to metastatic cancer, primary or metastatic brain tumors, chronic pain syndromes due to metastatic tumor, increased intracranial pressure, demyelinating diseases such as multiple sclerosis, neurodegenerative diseases such as Alzheimer's disease, inflammatory CNS disease, such as subacute sclerosing panencephalitis, and other related neurological disorders and diseases.

Another object of the present invention is to provide a TNF antagonist that can offer acute and chronic treatment regimens for neurological and related diseases. Examples of diseases in these categories include but are not limited to diseases of the central and peripheral nervous system such as Parkinson's disease, Bell's palsy, Guillain-Barre syndrome.

Another object of the present invention is to provide a TNF antagonist that can offer acute and chronic treatment for retinal and neuro-ophthalmic diseases. Examples of diseases in these categories include but are not limited to optic neuritis, macular degeneration and diabetic retinopathy.

Another object of the present invention is to provide a TNF antagonist that can offer acute and chronic treatment for muscular diseases and diseases of the neuromuscular junction. Examples of diseases in these categories include but are not limited to dermatomyositis, amyotrophic lateral sclerosis and muscular dystrophy.

Another object of the present invention is to provide a TNF antagonist that can offer acute and chronic treatment regimens for degenerative neurological disorders and neurologic disorders of uncertain etiology. Examples of diseases in these categories include but are not limited to Alzheimer's disease, Huntington's disease, and Creutzfeld-Jakob disease.

Another object of the present invention is to provide a TNF antagonist that can offer acute and chronic treatment regimens for neurologic injuries. Examples of diseases in these categories include but are not limited to acute spinal cord injury, acute brain injury, and stroke.

Another object of the present invention is to provide a TNF antagonist that can offer acute and chronic treatment regimens for inflammatory and autoimmune disorders of the nervous system, examples being subacute sclerosing panencephalitis and myasthenia gravis.

SUMMARY OF THE INVENTION

The present invention provides a method for inhibiting the action of TNF for treating neurological conditions in a human by administering a TNF antagonist for reducing the inflammation of neuronal tissue or the neuromuscular junction of a human, or for modulating the immune response affecting neuronal tissue or the neuromuscular junction of a human by administering to the human a therapeutically effective dosage level of a TNF antagonist. The TNF antagonist is selected from the group consisting of etanercept, infliximab, pegylated soluble TNF receptor Type I (PEGsTNF-R1), other agents containing soluble TNF receptors, CDP571 (a humanized monoclonal anti-TNF-alpha antibody), other monoclonal anti-TNF-alpha antibodies, TNF-alpha converting enzyme inhibitors and D2E7 (a human anti-TNF mAb) for reducing the inflammation of neuronal tissue or the neuromuscular junction of a human, or for modulating the immune response affecting neuronal tissue or the neuromuscular junction of a human. Additionally, other TNF antagonists are used for administering a therapeutically effective dosage level to a human wherein the TNF antagonist is selected from the group consisting of thalidomide, phosphodiesterase 4 (IV) inhibitor thalidomide analogues and other phosphodiesterase IV inhibitors for reducing the inflammation of neuronal tissue or the neuromuscular junction of a human, or for modulating the immune response affecting neuronal tissue or the neuromuscular junction of a human.

The present invention further provides a method for inhibiting the action of TNF for treating conditions of the optic nerve or retina in a human by administering a TNF antagonist for reducing the inflammation of the optic nerve or retina of a human, or for modulating the immune response affecting the optic nerve or retina of a human by administering a therapeutically effective dosage level to the human of a TNF antagonist. The TNF antagonist is selected from the aforementioned pharmacological products listed above.

The present invention also provides a method for inhibiting the action of TNF for treating muscular diseases in a human by administering a TNF antagonist for reducing the inflammation of muscle of a human, or for modulating the immune response affecting the muscle of a human by administering a therapeutically effective dosage level to the human of a TNF antagonist. The TNF antagonist is selected from the aforementioned pharmacological products listed above.

In the step of administering the TNF antagonist to a human, the TNF antagonist is performed through any of the following routes including subcutaneous, intravenous, intrathecal, intramuscular, intranasal, oral, transepidermal, parenteral, by inhalation, or intracerebroventricular.

DETAILED DESCRIPTION OF THE PREFERRED EMBODIMENT

TNF antagonist regimens to be used for treating disorders are designed in two general ways: acute regimens, designed to achieve rapid blood levels and rapid action, wherein the TNF blockade is desired for hours to days; and chronic regimens, wherein the TNF blockade is desired for days, weeks, or months. TNF antagonists which are suitable for these regimens are etanercept (ENBREL™) from Immunex Corporation; infliximab (REMICADE™) from Centocor, Inc.; pegylated soluble TNF Receptor Type I (PEGs TNF-R1); other agents containing soluble TNF receptors; CDP571 (a humanized monoclonal anti-TNF-alpha antibodies); other monoclonal anti-TNF-alpha antibodies; D2E7 (a human anti-TNF mAb); thalidomide; phosphodiesterase 4 (IV) inhibitor thalidomide analogues; other phosphodiesterase IV inhibitors; and TNF alpha converting enzyme inhibitors. Etanercept or infliximab may be used for the immediate, short term and long term (acute and chronic) blockade of TNF in order to minimize neurological damage mediated by TNF dependent processes occurring in the aforementioned "Neurologic and Related TNF Disorders". The use of these TNF antagonists or TNF blockers results in the amelioration of these physiological problems.

Trauma, injury, compression and other neurological disorders can affect individual nerves, nerve roots, the spinal cord, or the brain. The conditions which are of most concern in the present invention are the following:
1) acute spinal cord and brain injury,
2) demyelinating diseases, such as multiple sclerosis,
3) spinal cord compression due to metastatic cancer,
4) primary or metastatic brain tumors,
5) chronic pain syndromes due to metastatic tumor,
6) inflammatory CNS diseases, such as subacute sclerosing panencephalitis,
7) Alzheimer's disease,
8) Huntington's disease,
9) Creutzfeld-Jakob disease,
10) Parkinson's disease,
11) myasthenia gravis,
12) Guillain-Barre syndrome,
13) Bell's palsy,
14) diabetic neuropathy,
15) amyotrophic lateral sclerosis,
16) optic neuritis,
17) macular degeneration,
18) retinitis pigmentosa,
19) diabetic retinopathy,
20) muscular dystrophy, and
21) polymyositis-dermatomyositis.

TNF antagonists are a novel way to treat the above-listed disorders in comparison with steroids. Experimental evidence has shown that excessive levels of TNF are released by injury to neuronal tissue. Accordingly, the use of TNF antagonists will result in amelioration of these disorders and diseases. Because of the profoundly powerful action of the new TNF antagonists that have recently become available, these agents can provide treatment in a unique way, filling an urgent clinical need for more effective therapy. Also, because of the extremely safe side effect profile of these agents, they can be used either singly or in combination with other pharmacologic agents. TNF antagonists can also safely be used with steroids, which are the only other class of agents which have been shown to be beneficial for certain of these conditions. Importantly, the TNF antagonists lack the adverse effects of steroids as previously described. Lastly, steroids are only partially effective or completely ineffective.

The TNF antagonists may be administered by any of the following methods to treat the above-identified disorders: subcutaneous, intravenous, intrathecal, intramuscular, intranasal, oral, transepidermal, parenteral, by inhalation, or intracerebroventricular. Also, the dosage regimens for treatment are of 3 types:

Regimen 1: Acute Regimen

This regimen can be used to treat all of the disorders listed above, with any of the TNF antagonists listed above, and with any of the routes of administration listed above. This regimen may include just a single dose, or repeated doses up to and including 30 continuous days.

Regimen 2: Chronic Regimen

This regimen can be used to treat all of the disorders listed above, except for: acute spinal cord and brain injury, spinal cord compression, and Bell's palsy. Any of the TNF antagonists listed above may be used, and any of the routes of administration listed above may be used. This regimen includes repeated doses of 31 days or longer.

Regimen 3: Directly Into The CSF

This regimen may be used for acute, chronic or both regimens. There are two variations: either through the intrathecal route at the level of the spinal cord; or directly into the cerebroventricular system at the level of the brain. This regimen can be used to treat all of the disorders listed above, except for: myasthenia gravis, Bell's palsy, diabetic neuropathy, and amyotrophic lateral sclerosis.

More detailed discussion of each of these clinical conditions is as follows:

1) Acute Spinal Cord and Brain Injury

About 10,000 cases occur per year in the U.S., with a current population of over 200,000 patients with residual neurologic damage, many of whom are paralyzed (quadriplegia or paraplegia). Current treatment for the acute injury is inadequate. In the early 1990's it was shown that early (within 8 hours of injury) treatment with high doses of steroids (methyl prednisolone) was beneficial for some of these patients. Surgical stabilization and spinal decompression is often necessary because of excessive swelling (edema) which can itself cause further severe injury to the cord due to further compression of the cord against its bony spinal canal. The etiology of most of these cases are motor vehicle accidents, with the remainder being sports injuries, falls, and other accidents. The window of opportunity for treatment is small, since massive swelling can occur within minutes.

The treatment regimen used here would be the acute regimen. This could involve any of the TNF antagonists, but currently etanercept would be the leading candidate. Etanercept is currently approved only for rheumatoid arthritis, and is used as a subcutaneous injection of 25 mg given twice a week. This regimen produces peak blood levels in an average of 72 hours. Preferred methods for acute spinal cord or brain injury involve either administration directly into the CSF or through intravenous infusion producing a therapeutic effect more rapidly than can be produced by subcutaneous injection. These are new methods of dosing that are not being used for arthritis. These acute regimens are unique delivery methods for etanercept and are uniquely necessary for clinical neurologic conditions requiring rapid blockade of TNF.

Regimens 1 and 3, as outlined above, may be used to treat these disorders.

2) Demyelinating Disease, Such As Multiple Sclerosis

Demyelinating neurological diseases, the most important being multiple sclerosis, are inadequately treated by currently available therapies, and continue to produce progressive, severe, neurologic impairment in a large population of patients in the United States and worldwide. There is experimental evidence which documents the role of TNF in multiple sclerosis. There is a wide body of work which documents the role of both cellular and humoral immunity in multiple sclerosis. Using the above-listed TNF antagonists represents a novel approach to the treatment of these important disorders.

Several novel approaches are suggested. For acute demyelinating disease, it is paramount to use therapy which is rapidly effective to prevent permanent neurological damage. In this case, novel routes of administration of the TNF antagonists may be used. These novel routes include administration of etanercept or infliximab directly into the CSF; or intravenous administration of etanercept. For chronic forms of demyelinating disease, the more familiar routes of administration of etanercept (subcutaneous) or infliximab (intravenous) may be elected. These novel regimens are designed as such because of the complementary mechanisms of action and low toxicity of these biopharmaceutical agents.

Regimens 1, 2 and 3, as outlined above, may be used to treat these disorders.

3) Spinal Cord Compression Due to Metastatic Cancer

Cord compression due to metastatic cancer is a catastrophic event leading to rapid paralysis if not quickly diagnosed and treated. It is most common with cancers of the breast, colon, lung and prostate, but can be a complication of metastatic disease from a wide variety of malignancies, including melanoma and multiple myeloma. Current treatment regimens include high dose steroids, emergency radiation treatment, and/or emergent surgical decompression. Paralysis can occur within hours, so treatment must be initiated within this time period to avoid permanent sequelae. The mechanism of action of TNF blockage here would be similar to that above. In addition, it is possible that TNF blockade could be directly tumoricidal or tumoristatic with certain malignancies. Impending cord compression could be treated with the chronic regimen. However, as explained above, most patients would need to be emergently treated with the acute regimen, as outlined above.

Regimens 1 and 3, as outlined above, may be used to treat these disorders.

4) Primary or Metastatic Brain Tumors

Primary brain tumors can be either benign (most commonly meningioma) or malignant (usually gliomas). Metastatic brain tumors can be from any source, most commonly lung cancer, breast cancer, or other malignancies such as melanoma. Treatment for these tumors is primarily surgery or radiation, with generally poor response to chemotherapy. Many of these tumors cause surrounding edema which can cause further neurologic deterioration. TNF blockade, either the acute or chronic treatment regimen, would be beneficial while these patients are awaiting surgery. Additionally, TNF blockade, as discussed above, would have direct tumor inhibiting properties.

Regimens 1, 2 and 3, as outlined above, may be used to treat these disorders.

5) Chronic Pain Syndromes Due to Metastatic Tumor

Pain due to metastatic cancer is inadequately treated by currently used agents. It is probable that the mechanism of action of this pain is mediated in part by the overproduction of TNF. TNF blockade would be beneficial for selected tumors, particularly bone metastases where compression is involved. The chronic treatment regimens would be used. One general note of caution when treating malignancies is necessary: While TNF blockade is likely to have an antitumor effect with certain malignancies, it is also possible that TNF blockade could increase growth rates with certain malignancies.

Regimens 1, 2 and 3, as outlined above, may be used to treat these disorders.

6) Inflammatory CNS Diseases, Such As Subacute Sclerosing Panencephalitis

Subacute sclerosing panencephalitis is a rare inflammatory disease of the brain, secondary to infection with a measles virus.

Regimens 1, 2 and 3, as outlined above, may be used to treat these disorders.

7) Alzheimer's Disease

Alzheimer's disease is a common form of progressive dementia, of unknown cause and without an effective cure. It is characterized by neurofibrillary tangles and plaques on pathologic examination of brain tissue.

Regimens 1, 2 and 3, as outlined above, may be used to treat these disorders.

8) Huntington's Disease

Huntington's disease (Huntington's chorea) is a rare, progressive, fatal neurological disorder for which there is currently no effective treatment. It is often hereditary, and is characterized by a movement disorder (chorea), as well as progressive dementia.

Regimens 1, 2 and 3, as outlined above, may be used to treat these disorders.

9) Creutzfeld-Jakob Disease

Creutzfeld-Jakob disease, as well as New Variant Creuzfeld-Jakob disease, is one of the transmissible spongioform encephalopathies, along with Kuru and Scrapie and "Mad Cow Disease (Bovine spongioform encephalopathy)". These diseases are caused by infection with a new class of biologic agent called prions. These diseases are progressive, fatal, and can be contracted by ingesting tissue of an infected animal. There is no known treatment.

Regimens 1, 2 and 3, as outlined above, may be used to treat these disorders.

10) Parkinson's Disease

Parkinson's disease is a common neurologic disorder characterized by tremor, gait disorder, and dementia, for which there is no known cure.

Regimens 1, 2 and 3, as outlined above, may be used to treat these disorders.

11) Myasthenia Gravis

Myasthenia gravis is an autoimmune disorder of the neuromuscular junction, characterized by muscle weakness and easy fatiguability. There is no known cure. Corticosteroids are one of the mainstays of treatment.

Regimens 1 and 2, as outlined above, may be used to treat these disorders.

12) Guillain-Barre Syndrome

Guillain-Barre syndrome is characterized by the rapid onset of weakness, usually in an ascending distribution, and often culminating in difficulty breathing. It often follows a preceding viral infection.

Regimens 1, 2 and 3, as outlined above, may be used to treat these disorders.

13) Bell's Palsy

Bell's palsy is characterized by the sudden onset of hemifacial paralysis, caused by acute mononeuropathy of the seventh cranial nerve, the facial nerve. It can follow viral infection, vaccination, or may be idiopathic. The mainstay of treatment is large doses of corticosteroids.

Regimen 1, as outlined above, may be used to treat this disorder.

14) Diabetic Neuropathy

Diabetic neuropathy consists of a variety of clinical syndromes of neurologic damage occurring in patients with either juvenile onset or adult onset diabetes mellitus. Diabetic peripheral neuropathy causes sensory deficits, numbness, tingling, and painful paresthesias in the extremities. Diabetic autonomic neuropathy causes disorders of the autonomic nervous system, including diabetic gastropathy.

Regimens 1 and 2, as outlined above, may be used to treat these disorders.

15) Amyotrophic Lateral Sclerosis

Amyotrophic lateral sclerosis is a progressive fatal, neurologic disease causing progressive weakness and cranial nerve palsies, causing difficulty with speech, eye movements, and such. There is no known cure.

Regimens 1 and 2, as outlined above, may be used to treat these disorders.

16) Optic Neuritis

Optic neuritis is characterized by acute inflammation affecting the optic nerve, causing visual field defects. It is often part of Multiple Sclerosis, for which it may be the presenting symptom. Attacks can be intermittent and repeated.

Regimens 1, 2 and 3, as outlined above, may be used to treat these disorders.

17) Macular Degeneration

Macular degeneration is a leading cause of blindness, affecting predominantly the older population, for which there is no known cure.

Regimens 1, 2 and 3, as outlined above, may be used to treat these disorders.

18) Retinitis Pigmentosa

Retinitis pigmentosa is a hereditary retinal disease, resulting in blindness, for which there is no known cure.

Regimens 1, 2 and 3, as outlined above, may be used to treat these disorders.

19) Diabetic Retinopathy

Diabetic Retinopathy includes a spectrum of retinal disorders, including hemorrhage and exudates, which occur in patients with diabetes mellitus. Part of the retinopathy is due to a vascular damage caused by diabetes.

Regimens 1, 2 and 3, as outlined above, may be used to treat these disorders.

20) Muscular Dystrophy

Muscular dystrophy is a group of related diseases of muscle, many of which are hereditary, characterized by progressive muscular weakness. The cause and cure are unknown.

Regimens 1 and 2, as outlined above, may be used to treat these disorders.

21) Polymyositis—Dermatomyositis

Polymyositis is an autoimmune inflammatory disease of muscle, characterized by progressive proximal muscle weakness and muscle wasting. Pathology shows an intense inflammatory infiltrate in the muscle. Treatment includes immunosuppressive drugs, corticosteroids, and respiratory support for more advanced cases. Dermatomyositis is polymyositis with a characteristic accompanying skin rash.

Regimens 1 and 2, as outlined above, may be used to treat these disorders.

Methods of Administration and Dosage Levels

For treating the above diseases with the above mentioned TNF antagonists, these TNF antagonists may be administered by the following routes:

The above TNF antagonists may be administered subcutaneously in the human and the dosage level is in the range of 5 mg to 50 mg for acute or chronic regimens.

The above TNF antagonists may be administered intranasally in the human and the dosage level is in the range of 0.1 mg to 10 mg for acute or chronic regimens.

The above TNF antagonists may be administered intramuscularly in the human and the dosage level is in the range of 25 mg to 100 mg.

The above TNF antagonists may be administered intravenously in the human and the dosage level is in the range of 2.5 mg/kg to 20 mg/kg.

The above TNF antagonists may be administered intrathecally in the human and the dosage level is in the range of 0.1 mg to 25 mg administered from once a day to every three months.

The above TNF antagonists may be administered transepidermally in the human and the dosage level is in the range of 10 mg to 100 mg.

The above TNF antagonists may be administered by inhaling by the human and the dosage level is in the range of 0.2 mg to 40 mg.

The above TNF antagonists may be administered intracerebroventricularly in the human and the dosage level is in the range of 0.1 mg to 25 mg administered once a day to once every 3 month.

The above TNF antagonists may be administered orally by the human and the dosage level is in the range of 10 mg to 300 mg.

Etanercept is administered intramuscularly in a human wherein the dosage level is in the range of 25 mg to 100 mg.

Infliximab is administered intravenously in a human wherein the dosage level is in the range of 2.5 mg/kg to 20 mg/kg.

Etanercept is administered subcutaneously in a human wherein the dosage level is in the range of 5 mg to 50 mg.

Etanercept is administered intrathecally in a human wherein the dosage level is in the range of 0.1 mg to 25 mg administered from once a day to once a month.

Infliximab is administered intrathecally in a human wherein the dosage level is in the range of 0.1 mg/kg to 5 mg/kg administered from once a week to once every three months.

Etanercept is administered intracerebroventricularly in a human wherein the dosage level is in the range of 0.1 mg to 25 mg administered once a day to once a month.

Infliximab is administered intracerebroventricularly in a human wherein the dosage level is in the range of 0.1 mg/kg to 5 mg/kg administered once a week to once every 3 months.

The thalidomide group is administered orally by a human wherein the dosage level is in the range of 10 mg to 300 mg.

All antagonists and all routes of administration can be used for all of the above diseases with the following exceptions:

a) Etanercept and infliximab will only be used subcutaneously, intramuscularly, intraventricularly, or intrathecally, or intravenously.

b) Intracerebroventricular and intrathecal routes are more invasive, and will only be used with severe disorders, usually only with those that are fatal or devastating. As to the diseases and disorders discussed above, these routes are most suitable for acute brain and spinal cord injury; Alzheimer's disease; subacute sclerosing panencephalitis; Parkinson's disease; Huntington's disease; Creutzfeld-Jakob disease; amyotrophic lateral sclerosis; myasthenia gravis; optic neuritis; multiple sclerosis; macular degeneration, and retinitis pigmentosa. Excluded are diseases outside of the CNS, i.e. those involving muscle or peripheral nerves. These excluded diseases include diabetic neuropathy; Bell's palsy (too mild to justify this route), muscular dystrophies; and polymyositis.

c) All other routes should be specified for all of the diseases, except that the thalidomide group will not be used for diabetic neuropathy or for peripheral neuropathy.

Advantages of the Present Invention

Accordingly, an advantage of the present invention is that it provides TNF antagonists for a new pharmacologic treatment of "Neurologic and Related TNF Disorders", such that the use of these TNF antagonists will result in the amelioration of these conditions.

Another advantage of the present invention is that it provides for a TNF antagonist, for providing suppression and inhibition of the action of TNF in a human to treat "Neurologic and Related TNF Disorders".

Another advantage of the present invention is that it provides for a TNF antagonist that reduces inflammation to the patient by inhibiting the action of TNF in the human body for the immediate, short term (acute conditions) and long term (chronic conditions), such that this reduction in inflammation will produce clinical improvement in the patient and will give the patient a better opportunity to heal, slows disease progression, prevents neurological damage, or otherwise improves the patient's health.

Another advantage of the present invention is that it provides TNF antagonists that can offer acute and chronic treatment regimens for neurological conditions caused by neurological trauma, compression, injury and/or disease; such conditions including acute spinal cord injury, spinal cord compression due to metastatic cancer, primary or metastatic brain tumors, chronic pain syndromes due to metastatic tumor, increased intracranial pressure, demyelinating diseases such as multiple sclerosis, neurodegenerative diseases such as Alzheimer's disease, inflammatory CNS disease, such as subacute sclerosing panencephalitis, and other related neurological disorders and diseases.

Another advantage of the present invention is that it provides for a TNF antagonist that can offer acute and chronic treatment regimens for neurologic and related diseases. Examples of diseases in these categories include but are not limited to diseases of the central and peripheral nervous system such as Parkinson's disease, Bell's palsy, Guillain-Barre Syndrome.

Another advantage of the present invention is that it provides for a TNF antagonist that can offer acute and chronic treatment for retinal and neuro-ophthalmic diseases. Examples of diseases in these categories include but are not limited to optic neuritis, macular degeneration and diabetic retinopathy.

Another advantage of the present invention is that it provides for a TNF antagonist that can offer acute and chronic treatment for muscular diseases and diseases of the neuromuscular junction. Examples of diseases in these categories include but are not limited to dermatomyositis, amyotrophic lateral sclerosis and muscular dystrophy.

Another advantage of the present invention is that it provides for a TNF antagonist that can offer acute and chronic treatment regimens for degenerative neurologic disorders and neurologic disorders of uncertain etiology. Examples of diseases in these categories include but are not limited to Alzheimer's disease, Huntington's disease, and Creutzfeld-Jakob disease.

Another advantage of the present invention is that it provides for a TNF antagonist that can offer acute and chronic treatment regimens for neurologic injuries. Examples of diseases in these categories include but are not limited to acute spinal cord injury, acute brain injury, and stroke.

Another advantage of the present invention is that it provides for a TNF antagonist that can offer acute and chronic treatment regimens for inflammatory and autoimmune disorders of the nervous system, examples being subacute sclerosing panencephalitis and myasthenia gravis.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A method for inhibiting the action of TNF for treating neurological conditions in a human by administering a TNF antagonist for reducing the inflammation of neuronal tissue or the neuromuscular junction of said human, or for modulating the immune response affecting neuronal tissue or the neuromuscular junction of said human, comprising the step of:

a) administering a therapeutically effective dosage level to said human of said TNF antagonist selected from the group consisting of etanercept, infliximab, pegylated soluble TNF receptor Type I (PEGsTNF-R1), CDP571 (a humanized monoclonal anti-TNF-alpha antibody), and D2E7 (a human anti-TNF mAb) for reducing the inflammation of neuronal tissue or the neuromuscular junction of said human, or for modulating the immune response affecting neuronal tissue or the neuromuscular junction of said human.

2. A method for inhibiting the action of TNF in accordance with claim 1, wherein the step of administering said TNF antagonist is performed through any of the following routes: subcutaneous, intravenous, intrathecal, intramuscular, intranasal, oral, transepidermal, parenteral, by inhalation, or intracerebroventricular.

3. A method for inhibiting the action of TNF in accordance with claim 1, wherein the step of administering said dosage level is for treating neurodegenerative diseases including Alzheimer's disease, Huntington's disease and Creutzfeld-Jakob disease.

4. A method for inhibiting the action of TNF in accordance with claim 1, wherein the step of administering said dosage level is for treating Parkinson's disease.

5. A method for inhibiting the action of TNF in accordance with claim 1, wherein the step of administering said dosage level is for treating myasthenia gravis.

6. A method for inhibiting the action of TNF in accordance with claim 1, wherein the step of administering said dosage level is for treating Guillain-Barre syndrome.

7. A method for inhibiting the action of TNF in accordance with claim 1, wherein the step of administering said dosage level is for treating Bell's palsy.

8. A method for inhibiting the action of TNF in accordance with claim 1, wherein the step of administering said dosage level is for treating neurological traumas and injuries, and for treating neurological diseases and disorders.

9. A method for inhibiting the action of TNF in accordance with claim 1, wherein the step of administering said dosage level is for treating acute spinal cord or brain injury.

10. A method for inhibiting the action of TNF in accordance with claim 1, wherein the step of administering said dosage level is for treating primary or metastatic brain tumors.

11. A method for inhibiting the action of TNF in accordance with claim 1, wherein the step of administering said dosage level is for treating chronic pain syndrome due to metastatic tumor.

12. A method for inhibiting the action of TNF in accordance with claim 1, wherein the step of administering said dosage level is for treating peripheral neuropathies, including diabetic neuropathy.

13. A method for inhibiting the action of TNF in accordance with claim 1, wherein the step of administering said dosage level is for treating central nervous system lesions.

14. A method for inhibiting the action of TNF in accordance with claim 1, wherein the step of administering said dosage level is for treating autoimmune neurological diseases.

15. A method for inhibiting the action of TNF in accordance with claim 1, wherein the step of administering said dosage level is for treating multiple sclerosis.

16. A method for inhibiting the action of TNF in accordance with claim 1, wherein the step of administering said dosage level is for treating inflammatory CNS diseases including subacute sclerosing panencephalitis.

17. A method for inhibiting the action of TNF in accordance with claim 1, wherein the step of administering said dosage level is for treating amyotrophic lateral sclerosis.

18. A method for inhibiting the action of TNF in accordance with claim 1, wherein the step of administering said TNF antagonist is performed subcutaneously in said human wherein said dosage level is in the range of 5 mg to 50 mg for acute or chronic regimens.

19. A method for inhibiting the action of TNF in accordance with claim 1, wherein the step of administering said TNF antagonist is performed intranasally in said human wherein said dosage level is in the range of 0.1 mg to 10 mg for acute or chronic regimens.

20. A method for inhibiting the action of TNF in accordance with claim 1, wherein the step of administering said TNF antagonist in the form of etanercept is performed intramuscularly in said human wherein said dosage level is in the range of 25 mg to 100 mg.

21. A method for inhibiting the action of TNF in accordance with claim 1, wherein the step of administering said TNF antagonist in the form of infliximab is performed intravenously in said human wherein said dosage level is in the range of 2.5 mg/kg to 20 mg/kg.

22. A method for inhibiting the action of TNF in accordance with claim 1, wherein the step of administering said TNF antagonist in the form of etanercept is performed subcutaneously in said human wherein said dosage level is in the range of 5 mg to 50 mg.

23. A method for inhibiting the action of TNF in accordance with claim 1, wherein the step of administering said TNF antagonist in the form of etanercept is performed intrathecally in said human wherein said dosage level is in the range of 0.1 mg to 25 mg administered from once a day to once every three months.

24. A method for inhibiting the action of TNF in accordance with claim 1, wherein the step of administering said TNF antagonist in the form of infliximab is performed intrathecally in said human wherein said dosage level is in the range of 0.1 mg/kg to 5 mg/kg administered from once a week to once every three months.

25. A method for inhibiting the action of TNF in accordance with claim 1, wherein the step of administering said TNF antagonist is performed transepidermally in said human wherein said dosage level is in the range of 10 mg to 100 mg.

26. A method for inhibiting the action of TNF in accordance with claim 1, wherein the step of administering said TNF antagonist is performed by inhaling in said human wherein said dosage level is in the range of 0.2 mg to 40 mg.

27. A method for inhibiting the action of TNF in accordance with claim 1, wherein the step of administering said TNF antagonist is performed intravenously in said human wherein said dosage level is a therapeutically effective amount.

28. A method for inhibiting the action of TNF in accordance with claim 1, wherein the step of administering said TNF antagonist in the form of etanercept is performed intracerebroventricularly in said human wherein said dosage level is in the range of 0.1 mg to 25 mg administered once a day to once a month.

29. A method for inhibiting the action of TNF in accordance with claim 1, wherein the step of administering said TNF antagonist in the form of infliximab is performed intracerebroventricularly in said human wherein said dosage level is in the range of 0.1 mg/kg to 5 mg/kg administered once a week to once every 3 months.

* * * * *

UNITED STATES PATENT AND TRADEMARK OFFICE
CERTIFICATE OF CORRECTION

PATENT NO. : 6,177,077
DATED : January 23, 2001
INVENTOR(S) : EDWARD L. TOBINICK It is certified that error appears in the above-identified patent and that said Letters Patent is hereby corrected as shown below:

Page 1, at Field (54), change "TNT" to --TNF--.

Page 1, at Field (76), Inventor: after "EDWARD L. TOBINICK", insert --M.D.--.

Signed and Sealed this

Fifteenth Day of May, 2001

Attest:

NICHOLAS P. GODICI

Attesting Officer     Acting Director of the United States Patent and Trademark Office